(12) United States Patent
Kloor et al.

(10) Patent No.: US 9,770,499 B2
(45) Date of Patent: Sep. 26, 2017

(54) MSI-SPECIFIC FRAMESHIFT PEPTIDES (FSP) FOR PREVENTION AND TREATMENT OF CANCER

(71) Applicant: Ruprecht-Karls-Universitat Heidelberg, Heidelberg (DE)

(72) Inventors: Matthias Kloor, Ludwigshafen (DE); Miriam Reuschenbach, Heidelberg (DE); Magnus von Knebel-Doeberitz, Heidelberg (DE)

(73) Assignee: Ruprecht-Karls-Universitat Heidelberg, Heidelberg (DE)

( * ) Notice: Subject to any disclaimer, the term of this patent is extended or adjusted under 35 U.S.C. 154(b) by 10 days.

(21) Appl. No.: 14/926,329

(22) Filed: Oct. 29, 2015

(65) Prior Publication Data

US 2016/0038579 A1    Feb. 11, 2016

Related U.S. Application Data

(62) Division of application No. 13/713,753, filed on Dec. 13, 2012, now Pat. No. 9,205,140.

(51) Int. Cl.
*A61K 38/00* (2006.01)
*A61K 39/00* (2006.01)
*C07K 1/00* (2006.01)

(52) U.S. Cl.
CPC .... *A61K 39/0011* (2013.01); *A61K 2039/572* (2013.01); *A61K 2039/70* (2013.01)

(58) Field of Classification Search
None
See application file for complete search history.

(56) References Cited

U.S. PATENT DOCUMENTS

2005/0239070 A1   10/2005   Von Knebel-Doeberitz

FOREIGN PATENT DOCUMENTS

WO    WO 99/58552    11/1999
WO    WO 03/087162    10/2003

OTHER PUBLICATIONS

Li et al. (Vaccines, 2014, 2:515-536).*
Kloor et al., "Immune Evasion of Microsatellite Unstable Colorectal Cancers," International Journal of Cancer, 127:1001-1010, 2010.
Linnebacher et al., "Frameshift Peptide-Derived T-Cell Epitopes: A Source of Novel Tumor-Specific Antigens" International Journal of Cancer, 93:6-11, 2001.
Rueschenbach et al., "Serum Antibodies Against Frameshift Peptides in Microsatellite Unstable Colorectal Cancer Patients with Lynch Syndrome" Familial Cancer 9:173-179, 2010.
Ripberger et al., "Identification of an HLA-A0201-Restricted CTL Epitope Generated by a Tumor-Specific Frameshift Mutation in a Coding Microsatellite of the OGT Gene" Journal of Clinical Immunology, 23(5):415-423, Sep. 2003.
Schwitalle et al., "Immunogenic peptides generated by frameshift mutations in DNA mismatch repair-deficient cancer cells" Cancer Immunity 4:14, Nov. 2004.
Schwitalle et al., "Immune Response Against Frameshift-Induced Neopeptides in HNPCC Patients and Healthy HNPCC Mutation Carriers," Gastroenterology, 134:988-997, 2008.
Tougeron, et al. "Tumor-infiltrating lymphocytes in colorectal cancers with microsatellite instability are correlated with the number and spectrum frameshit mutations," Modern Pathology, 22:1186-1195, 2009.

* cited by examiner

*Primary Examiner* — Julie Wu
(74) *Attorney, Agent, or Firm* — Vedder Price P.C.; Thomas J. Kowalski; Deborah L. Lu (57) ABSTRACT

Described is a vaccine for prevention and treatment of cancer characterized by microsatellite instability (MSI). The vaccine contains an MSI-specific frameshift peptide (FSP) generating humoral and cellular responses against tumor cells or a nucleic acid encoding said FSP. The vaccine of the present invention is particularly useful for the prevention/treatment of colorectal cancer, endometrial cancer, gastric cancer or small bowel cancer.

7 Claims, 3 Drawing Sheets
(2 of 3 Drawing Sheet(s) Filed in Color)

|  | AIM2(-1) | TAF1B(-1) | HT001(-1) | TGFBR2(-1) |
|---|---|---|---|---|
| patients: n=69 | 10.1% | 13.0% | 8.7% | 14.0% |
| healthy mutation carriers: n=31 | 9.7% | 12.9% | 3.2% | 11.1% |
| healthy controls: n=52 | 9.6% | 3.8% | 15.4% | 5.8% |

MSI-SPECIFIC FRAMESHIFT PEPTIDES (FSP) FOR PREVENTION AND TREATMENT OF CANCER

RELATED APPLICATIONS AND INCORPORATION BY REFERENCE

This application is a divisional of U.S. application Ser. No. 13/713,753, filed on Dec. 13, 2012.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Jul. 25, 2014, is named 45490.00.2001_SL.txt and is 4,365 bytes in size.

FIELD OF THE INVENTION

The present invention provides a vaccine for prevention and treatment of cancer characterized by microsatellite instability (MSI). The vaccine may contain an MSI-specific frameshift peptide (FSP) generating humoral and cellular responses against tumor cells or a nucleic acid encoding said FSP.

BACKGROUND OF THE INVENTION

Human tumors develop through two major pathways of genome instability, chromosomal instability and microsatellite instability (MSI) that results from defects in the DNA mismatch repair system. MSI is encountered in 15% of colorectal cancers and a variety of extracolonic malignancies showing a deficient DNA mismatch repair system, including endometrial cancers, gastric cancers, small bowel cancers and tumors of other organs. MSI cancers may develop sporadically or in the context of a hereditary tumor syndrome, hereditary non-polyposis colorectal cancer (HNPCC) or Lynch syndrome.

Figure 1A:
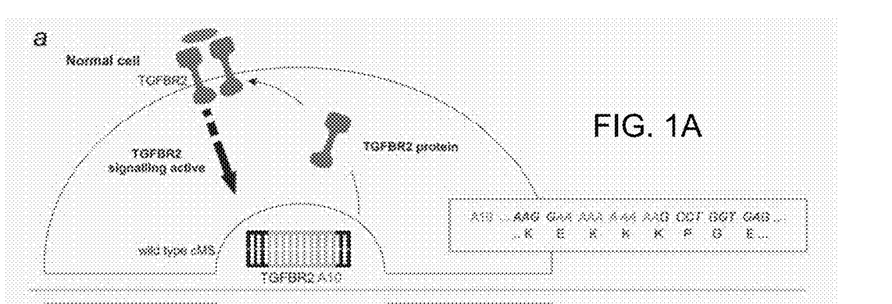
FIGS. 1A-1B: Schematic illustration of coding microsatellite instability resulting from DNA mismatch repair deficiency (Kloor et al., 2010)
Figure 1B:
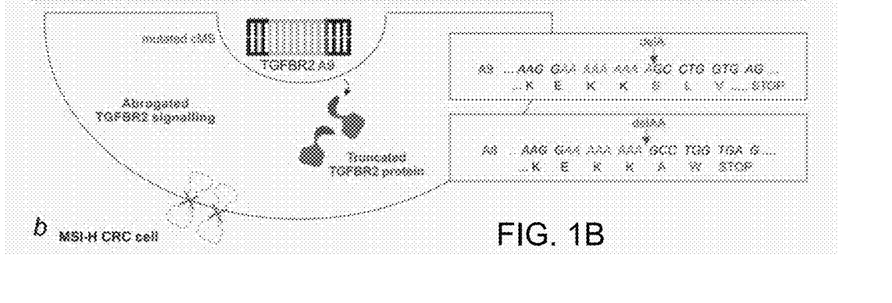

MSI colorectal cancers are characterized by a high immunogenicity that results from the generation of numerous frameshift peptides (FSP) during the development of MSI tumors as a direct result of mismatch repair deficiency leading to alterations of the translational reading frame when microsatellites in gene-encoding regions are affected by mutation (FIG. 1).

The abundance of predictable MSI-specific FSP antigens and the fact that they directly result from the malignant transformation process render FSP highly promising targets for immune therapy. It is believed that the human immune system is a potential resource to eradicate tumor cells and that effective treatment can be developed if the components of the immune system are properly stimulated to recognize and eliminate cancer cells. Thus, immunotherapy, which may comprise compositions and methods to activate the body's immune system, either directly or indirectly, to shrink or eradicate cancer, has been studied for many years as an adjunct to conventional cancer therapy.

It is generally admitted that the growth and metastasis of tumors depends largely on their capacity to evade host immune surveillance. Most tumors express antigens that can be recognized to a variable extent by the host immune system, but in many cases, the immune response is inadequate. Failure to elicit a strong activation of effector T-cells may result from the weak immunogenicity of tumor antigens or inappropriate or absent expression of co-stimulatory molecules by tumor cells. For most T-cells, production of IL-2 and proliferation require a co-stimulatory signal simultaneous with TCR engagement, otherwise, T-cells may enter a functionally unresponsive state, known as clonal anergy.

In spite of the length of time that these therapies have been investigated, there remains a need for improved strategies for enhancing the immune response against the tumor antigens.

Citation or identification of any document in this application is not an admission that such document is available as prior art to the present invention.

SUMMARY OF THE INVENTION

There is a need in the art for safe and effective compositions that can stimulate the immune system as a cancer immunotherapy.

According to the invention, safe and effective stimulation of the immune system as a cancer immunotherapy is achieved by the subject matters defined in the claims. In vitro data showed that FSP are highly immunogenic and can elicit pronounced FSP-specific T cell responses in vitro (Linnebacher et al. 2001, Ripberger et al. 2003, Schwitalle et al. 2004). In further studies examining peripheral blood drawn from patients with MSI colon cancer, a high frequency of FSP-specific T cell responses was demonstrated (Schwitalle et al. 2008). In spite of the high number of FSP-specific T cells in the tumor and in the peripheral blood, these patients showed no signs of autoimmunity, suggesting that FSP vaccination approaches are not expected to have side effects in terms of autoimmunity.

Immunological analyses in individuals carrying a germ line mutation in DNA mismatch repair genes predisposing to hereditary non-polyposis colorectal cancer (HNPCC) were also found to exhibit cellular immune responses against FSP, even in the absence of a clinically detectable tumor. This suggests that FSP-specific immune responses may be protective in HNPCC individuals, suggesting that FSP vaccination may also be used in a preventive setting as the first specific prevention approach in an inherited cancer condition.

In summary:
(a) Frameshift peptides (FSP) are MSI-specific and directly result from MSI tumor pathogenesis;
(b) No clinically relevant side effects are expected;
(c) Combinations of FSPs are predicted to target all tumors with MSI;
(d) FSP vaccination has been designed for therapy of 15% of colon cancers and tumors of the endometrium, stomach, small intestine and other organs;
(e) Molecular tumor analysis can identify patients that may benefit from FSP vaccination (targeted therapy); and
(f) FSP vaccination may be used as a preventive vaccination in high risk groups.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

Truncated proteins encompassing FSP sequences (red) are generated when coding microsatellite mutations lead to alterations of the translational reading frame (example: TGFBR2 protein). FIGS. 1A-1B disclose SEQ ID NOS 6-11, respectively, in order of appearance

ELISA revealed FSP-specific antibody responses directed against neopeptides derived from AIM2(-1), HT001(-1), TAF1B(-1), and TGFBR2(-1). Peptide specificity was demonstrated by preabsorption of respective serum antibodies as described previously (Reuschenbach et al., 2008).

FIGS. 4A-4B: Cytotoxic responses as determined by CD107a surface expression (A) Significant FSP-specific responses were observed in different healthy donors after stimulation of T cells with the antigen for four weeks. Responses did only occur in the presence of antigen-presenting B cells and the FSP antigen. Representative responses are shown in bar graphs.

(B) representative FACS analysis of CD107a assay for T cells incubated with B cells as antigen-presenting cells in the absence (left panel) or presence (right panel) of the FSP antigen HT001(-1).

DETAILED DESCRIPTION OF THE INVENTION

Thus, the present invention provides a vaccine containing an MSI tumor specific frameshift peptide (FSP), e.g., derived from TAF1B (Acc. No. L39061), HT001 (Acc. No. AF113539), AIM2 (Acc. No. AF024714), or TGFBR2 (Acc. No. NM_003242) or a nucleic acid encoding said FSP wherein said FSP is capable of eliciting an immune response against cancer showing MSI.

In a preferred embodiment, the vaccine of the present invention contains:

(a) an FSP which may comprise or consist of the following amino acid sequence:

```
                                              (TAF1B(-1))
                                             (SEQ ID NO: 1)
NTQIKALNRGLKKKTILKKAGIGMCVKVSSIFFINKQKP;

(HT001(-1))
                                             (SEQ ID NO: 2)
EIFLPKGRSNSKKKGRRNRIPAVLRTEGEPLHTPSVGMRETTGLGC;

(AIM2(-1))
                                             (SEQ ID NO: 3)
HSTIKVIKAKKKHREVKRTNSSQLV;
Or (TGFBR2(-1))
                                             (SEQ ID NO: 4)
ASPKCIMKEKKSLVRLSSCVPVALMSAMTTSSSQKNITPAILTCC;
```

(b) a functional equivalent of an FSP of (b); or
(c) a combination of the FSP of (a) and/or (b).

The term "functional equivalent" as used herein relates to, e.g., variants or fragments of the FSP which are still capable of eliciting an immune response against the cancer, i.e., are still useful as an efficient vaccine. An immune response is defined as a condition fulfilling at least one of the following criteria: 1. The induction of CD8-positive T cells, as detectable by cytotoxicity assays or IFN-gamma secretion or perforin expression or granzyme B expression or other cytokines that may be produced by CD8-positive T cells, measurable as above background by ELISpot or intracellular cytokine staining or cytokine ELISA or equivalent methods. 2. The induction of CD4-positive T cells, as detectable by cytokine secretion measurable as above background by ELISpot or intracellular cytokine staining or cytokine ELISA or equivalent methods. Cytokines may comprise IFN-alpha, IFN-gamma, IL-2, IL-4, IL-5, IL-6, IL-10, IL-12, IL-13, IL-17, TNF-alpha, TGF-beta or other cytokines that may be produced by CD4-positive T cells. 3. The induction of antibodies, as detectable by Western blot, ELISA and equivalent or related methods. 4. The induction of any kind of cellular Immune response not mediated by CD8-positive or CD4-positive T cells as described in 1 and 2.

The variants are characterized by amino acid deletions, substitutions, and/or additions. Preferably, amino acid differences are due to one or more conservative amino acid substitutions. The term "conservative amino acid substitutions" involves replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

For the generation of peptides showing a particular degree of identity to the FSP, e.g., genetic engineering may be used to introduce amino acid changes at specific positions of a cloned DNA sequence to identify regions critical for peptide function. For example, site directed mutagenesis or alanine-scanning mutagenesis (introduction of single alanine mutations at every residue in the molecule) may be used (Cunningham and Wells, 1989). The resulting mutant molecules may then be tested for immunogenicity using the assay of Example 1.

Preferably, the variants are characterized by not more than 8 aa, more preferably by not more than 6 aa and, even more preferably, by not more than 4 aa substitutions, deletions and/or additions.

In the fragment of an FSP at least 5 contiguous aa, preferably at least 10 contiguous aa, more preferably at least contiguous 15 aa and even more preferably at least 20 contiguous aa of the particular amino acid sequence are left. The fragment is still capable of eliciting an immune response.

In a more preferred embodiment, the vaccine of the present invention additionally comprises an adjuvant and/or immunostimulatory cytokine or chemokine.

Suitable adjuvants include an aluminium salt such as aluminium hydroxide gel (alum) or aluminium phosphate, but may also be a salt of calcium, iron or zinc, or may be an insoluble suspension of acylated tyrosine, or acylated sugars, cationically or anionicaily derivatised polysaccharides, or polyphosphazenes. Other known adjuvants include CpG containing oligonucleotides. The oligonucleotides are characterised in that the CpG dinucleotide is unmethylated. Such oligonucleotides are well known and are described in, for example WO 96/02555.

The use of immunostimulatory cytokines has become an increasingly promising approach in cancer immunotherapy. The major goal is the activation of tumour-specific T lymphocytes capable of rejecting tumour cells from patients with low tumour burden or to protect patients from a recurrence of the disease. Strategies that provide high levels of immunostimulatory cytokines locally at the site of antigen have demonstrated pre-clinical and clinical efficacy. Preferred immunostimulatory cytokines comprise IL-2, IL-4, IL-7, IL-12, IFNs, GM-CSF and TNF-α.

Chemokines are small (7-16 kD), secreted, and structurally related soluble proteins that are involved in leukocyte and dendritic cell chemotaxis, PMN degranulation, and angiogenesis. Chemokines are produced during the initial phase of host response to injury, allergens, antigens, or invading microorganisms. Chemokines selectively attract leukocytes to inflammatory foci, inducing both cell migration and activation. Chemokines may enhance innate or specific host immunity against tumors and, thus may also be useful in combination with an FSP.

The vaccine of the present invention might also contain a nucleic acid encoding the FSP for DNA immunization, a technique used to efficiently stimulate humoral and cellular immune responses to protein antigens. The direct injection of genetic material into a living host causes a small amount of its cells to produce the introduced gene products. This inappropriate gene expression within the host has important immunological consequences, resulting in the specific immune activation of the host against the gene delivered antigen. Direct injection of naked plasmid DNA induces strong immune responses to the antigen encoded by the gene vaccine. Once the plasmid DNA construct is injected the host cells take up the foreign DNA, expressing the viral gene and producing the FSP inside the cell. This form of antigen presentation and processing induces both MHC and class I and class II restricted cellular and humoral immune responses. The DNA vaccines are composed of vectors normally containing two unites: the antigen expression unit composed of promoter/enhancer sequences, followed by antigen (FSP)-encoding and polyadenylation sequences and the production unit composed of sequences necessary for vector amplification and selection. The construction of vectors with vaccine inserts is accomplished using recombinant DNA technology and the person skilled in the art knows vectors that may be used for this approach. The efficiency of DNA immunization may be improved by stabilising DNA against degradation, and increasing the efficiency of delivery of DNA into antigen presenting cells. This has been demonstrated by coating biodegradable cationic microparticles (such as poly(lactide-co-glycolide) formulated with cetyltrimethylammonium bromide) with DNA. Such DNA-coated microparticles may be as effective at raising CTL as recombinant vaccinia viruses, especially when mixed with alum. Particles 300 nm in diameter appear to be most efficient for uptake by antigen presenting cells.

A variety of expression vectors, e.g., plasmids or viral vectors, may be utilised to contain and express nucleic acid sequences encoding an FSP of the present invention.

A preferred viral vector is a poxvirus, adenovirus, retrovirus, herpesvirus or adeno-associated virus (AAV). Particularly preferred poxviruses are a vaccinia virus, NYVAC, avipox virus, canarypox virus, ALVAC, ALVAC(2), fowlpox virus or TROVAC.

Recombinant alphavirus-based vectors have also been used to improve DNA vaccination efficiency. The gene encoding the FSP is inserted into the alphavirus replicon, replacing structural genes but leaving non-structural replicase genes intact. The Sindbis virus and Semliki Forest virus have been used to build recombinant alphavirus replicons. Unlike conventional DNA vaccinations, however, alphavirus vectors are only transiently expressed. Alphavirus replicons raise an immune response due to the high levels of protein expressed by this vector, replicon-induced cytokine responses, or replicon-induced apoptosis leading to enhanced antigen uptake by dendritic cells.

In a further preferred embodiment, the FSP contains a Tag sequence, preferably at the C-terminus which might be useful for purification of a recombinantly produced FSP. A preferred Tag sequence is a His-Tag. A particularly preferred His-Tag consists of 6 His-residues (SEQ ID NO: 5).

The vaccine of the present invention is administered in an amount suitable for immunization of an individual and, preferably, additionally contains one or more common auxiliary agents. The employed term "amount suitable for immunization of an individual" comprises any amount of FSP with which an individual may be immunized. The amount depends on whether immunization is intended as a prophylactic or therapeutic treatment. In addition, the individual's age, sex and weight play a role for determining the amount. Thus, the amount suitable for immunization of an individual refers to amounts of the active ingredients that are sufficient to affect the course and the severity of the tumor, leading to the reduction or remission of such pathology. An ""amount suitable for immunization of an individual" may be determined using methods known to one skilled in the art (see for example, Fingl et al., 1975). The term "individual" as used herein comprises an individual of any kind and being able to fall ill with carcinomas. Examples of such individuals are humans and animals as well as cells thereof.

The administration of the vaccine by injection may be made at various sites of the individual intramuscularly, subcutaneously, intradermally or in any other form of application. It may also be favourable to carry out one or more "booster injections" having about equal amounts.

The employed term "common auxiliary agents" comprises any auxiliary agents suitable for a vaccine to immunize an individual. Such auxiliary agents are, e.g., buffered common salt solutions, water, emulsions, such as oil/water emulsions, wetting agents, sterile solutions, etc.

An FSP, nucleic acid sequence or vector of the present invention may be present in the vaccine as such or in combination with carriers. It is favourable for the carriers in the individual not to be immunogenic. Such carriers may be the individual's own proteins or foreign proteins or fragments thereof. Carriers, such as serum albumin, fibrinogen or transferrin or a fragment thereof are preferred.

The vaccine of the present invention may be therapeutic, that is, the compounds are administered to treat an existing cancer, or to prevent the recurrence of a cancer, or prophylactic, that is, the compounds are administered to prevent or delay the development of cancer. If the compositions are used therapeutically, they are administered to cancer patients and are designed to elicit an immune response to stabilize a tumor by preventing or slowing the growth of the existing cancer, to prevent the spread of a tumor or of metastases, to reduce the tumor size, to prevent the recurrence of treated cancer, or to eliminate cancer cells not killed by earlier treatments. A vaccine used as a prophylactic treatment is administered to individuals who do not have cancer, and are designed to elicit an immune response to target potential cancer cells.

The present invention also relates to the use of an FSP or functional equivalent, nucleic acid sequence or vector as defined above for the production of a vaccine for the prevention of a carcinoma, e.g., preventive vaccination of a high risk group, or treatment of a carcinoma. For example, these may be a colorectal cancer, preferably a hereditary non-polyposis colorectal cacner (HNPCC), an endometrial cancer, a gastric cancer or small bowel cancer.

By means of the present invention it is possible to immunize individuals, in particular humans and animals. Immunization takes place by both induction of antibodies and stimulation of CD8+ T cells. Thus, it is possible to take prophylactic and therapeutic steps against carcinomas.

The below examples explain the invention in more detail.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Detection of FSP-Specific T Cells in Peripheral Blood from Patients with MSI Colon Cancer and Healthy HNPCC Mutation Carriers (A) Methods (ELISpot Assay)

Frequencies of FSP-specific peripheral T cells (pTc) were quantified by determining the number of specific IFN-gamma-secreting Tc against newly designed FSPs derived from 3 cMS-containing candidate genes using ELISpot analysis. ELISpot assays were performed using 96-well nitrocellulose plates (Multiscreen; Millipore, Bedford, Mass.) coated overnight with mouse anti-human IFN-gamma monoclonal antibodies (mAb) (Mabtech, Nacka, Sweden) and blocked with serum containing medium. PTc (day 0, 1×105/well) were plated 6-fold with autologous CD40-activated B cells (4×10$^4$/well, TiBc or pBc, respectively) as antigen-presenting cells in 200 µl IMDM with 10% human AB serum. Peptides were added at a final concentration of 10 µg/mL. As a positive control, pTc were treated with 20 nmol/L phorbol-12-myristate-13-acetate in combination 350 nmol/L ionomycin. After incubation for 24 hours at 37° C., plates were washed thoroughly, incubated with biotinylated rabbit anti-human IFN-gamma mAb for 4 hours, washed again, and incubated with streptavidin-alkaline phosphatase for 2 hours, followed by a final wash step. Spots were detected by incubation with NBT/BCIP (Sigma-Aldrich) for 1 hour, reaction was stopped with water, and, after drying, spots were counted microscopically. Methods have been described in detail in Schwitalle et al., 2008.

(B) Results

To examine whether FSP-specific T cell responses were detectable in the peripheral blood of MSI-H CRC patients, ELISpot analyses were performed. Autologous pBc, which showed high expression of MHC class I and II, and costimulators (CD40, CD80, and CD86) as well as B-cell-specific antigens (CD19 and CD23) were used as antigen-presenting cells.

Pronounced reactivities were observed against newly designed FSPs derived from AIM2(-1), HT001(-1), TAF1B(-1), and TGFBR2(-1):

```
TAF1B(-1)
                                        (SEQ ID NO: 1)
NTQIKALNRGLKKKTILKKAGIGMCVKVSSIFFINKQKP

HT001(-1)
                                        (SEQ ID NO: 2)
EIFLPKGRSNSKKKGRRNRIPAVLRTEGEPLHTPSVGMRETTGLGC

AIM2(-1)
                                        (SEQ ID NO: 3)
HSTIKVIKAKKKHREVKRTNSSQLV

TGFBR2(-1)
                                        (SEQ ID NO: 4)
ASPKCIMKEKKSLVRLSSCVPVALMSAMTTSSSQKNITPAILTCC
(neopeptide sequences are underlined)
```

Figure 2:
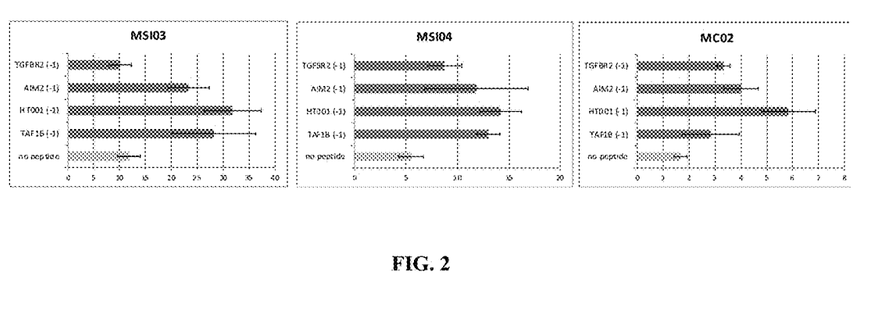
FIG. 2: Exemplary T cell responses against newly designed FSPs in peripheral blood from three patients with MSI colon cancer

The results obtained from patients (n=8) are summarized in Table 1. Representative ELISpot results are shown in FIG. 2.

TABLE 1

| | FSP-specific T cell responses against FSPs | | | | |
|---|---|---|---|---|---|
| Patient ID | no peptide | TAF1B (-1) | HT001 (-1) | AIM2 (-1) | TGFBR2 (-1) |
| MSI01 | 4 | 8.17 | 5.83 | 3.5 | 6 |
| MSI02 | 1.5 | 4.83 | 7.33 | 7.17 | 1.2 |
| MSI03 | 11.83 | 28.17 | 31.83 | 23.33 | 10.16 |
| MSI04 | 5.5 | 13 | 14.17 | 11.83 | 8.75 |
| MSI05 | 3 | 7.75 | 16 | 10 | 2.8 |
| MSI06 | 3.17 | 12 | 12.33 | 13.83 | 5.2 |

TABLE 1-continued

FSP-specific T cell responses against FSPs

| Patient ID | no peptide | TAF1B (-1) | HT001 (-1) | AIM2 (-1) | TGFBR2 (-1) |
|---|---|---|---|---|---|
| MSI07 | 6 | 17 | 16.83 | 14.5 | 9.33 |
| MC01 | 1.17 | 3.5 | 3.5 | 3 | 8 |
| MC02 | 1.67 | 2.83 | 5.83 | 4 | 3.33 |
| MC03 | 0.83 | 1.17 | 1.17 | 2.17 | 4.4 |
| MC04 | 15.17 | 18.83 | 18.67 | 15.17 | 20.75 |
| MC05 | 0.33 | 3.17 | 2.17 | 1.33 | 5.67 |
| MC06 | 30.5 | 37.83 | 37.8 | 34.83 | 39.5 |

Mean spot numbers from replicate analyses are given for each peptide and tested individual. MSI01-MSI07—patients with MSI-H CRC, MC01-MC06—healthy HNPCC germ line mutation carrier.

Example 2

Detection of FSP-Specific Humoral Immune Responses in Peripheral Blood from Patients with MSI Colon Cancer and Healthy HNPCC Mutation Carriers (A) Methods (ELISA)

For enzyme-linked immunosorbent assay (ELISA), peptides were coated to 96 well polystyrol microtiter plates "Maxisorp"' (Nunc, Roskilde, Denmark) at a concentration of 40 µg/ml in PBS overnight at 4° C. After coating, plates were washed 4 times with PBS (0.05% Tween) and blocked for 1 h with 0.5% casein in PBS. Peptide binding to the microtiter plates and optimal saturating peptide concentration were assessed using an alkaline phosphatase-peptide competition assay. To monitor individual background reactivity of each serum, a control peptide derived from the p16INK4a protein (p16_76-105) was used, against which no antibody reactivity was found in a large cohort of individuals (Reuschenbach et al., 2008). Each serum was diluted 1:100 in blocking buffer (0.5% casein in PBS) and tested in duplicates for the presence of antibodies against all FSPs and the control peptide. As a reference for inter-plate variance, one control serum was included on every plate, and peptide specific ODs of the control serum were used for normalization. Diluted sera (50 µl/well) were incubated for 1 h, and after a wash step plates were incubated with HRP-labeled rabbit anti-human-IgG antibody (Jackson Immunoresearch, West Grove, Pa.; 1:10,000 in blocking buffer) for 1 h. After washing, 50 µl/well of TMB substrate (Sigma, Deisenhofen, Germany) was added and the enzyme reaction was stopped after 30 minutes by adding 50 µl/well of 1 N H2SO4. Absorption was measured at 450 nm (reference wavelength 595 nm). Pre-absorption of serum antibodies for specificity control was done according to the method described in detail in Reuschenbach et al., 2008.

(B) Results

Figure 3:
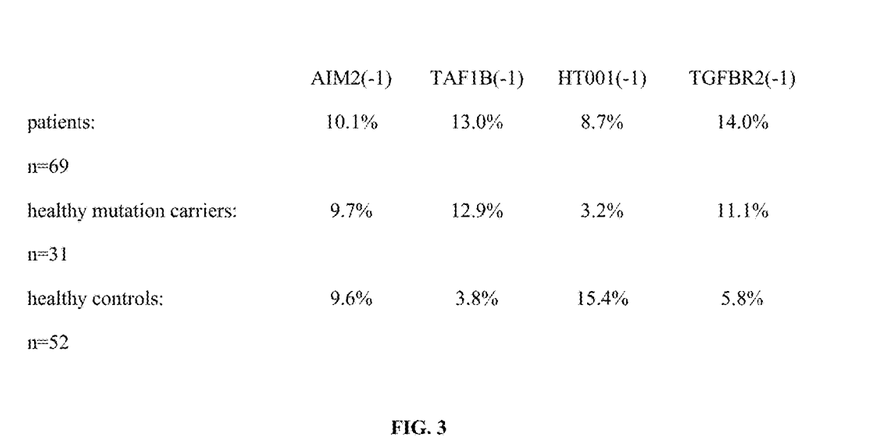
FIG. 3: Humoral immune responses against FSPs derived from AIM2(-1), HT001(-1), TAF1B(-1), and TGFBR2(-1)

To examine whether FSP-specific antibodies were detectable in the peripheral blood of MSI-H CRC patients, healthy Lynch syndrome mutation carriers, and healthy controls ELISA analyses were performed. Pronounced reactivities were observed against newly designed FSPs derived from AIM2(-1), HT001(-1), TAF1B(-1), and TGFBR2(-1). ELISA results are shown in FIG. 3.

Example 3

Detection of FSP-Specific Cytotoxic T Cell Responses

CD107a surface expression on T effector cells upon stimulation with the clinical FSP antigens was measured. CD107a assays are used to demonstrate secretion of cytotoxic granula containing perforin/granzyme B from effector cells. CD107a molecules are expressed on the surface of cytotoxic granula and become detectable on the cell surface if granula are released in the context of a cytotoxic T cell response.

To determine the potential of the FSP peptides to induce a cytotoxic cellular immune response, blood was drawn from healthy donors, and T cells were stimulated with the FSPs using dendritic cells as antigen-presenting cells. Stimulation was repeated weekly and over a time span of four weeks. After four weeks, T cells were harvested and coincubated with target cells and FSPs CD107a assay was used to analyze peptide-specific induction of a cytotoxic T cell response.

Figure 4A:
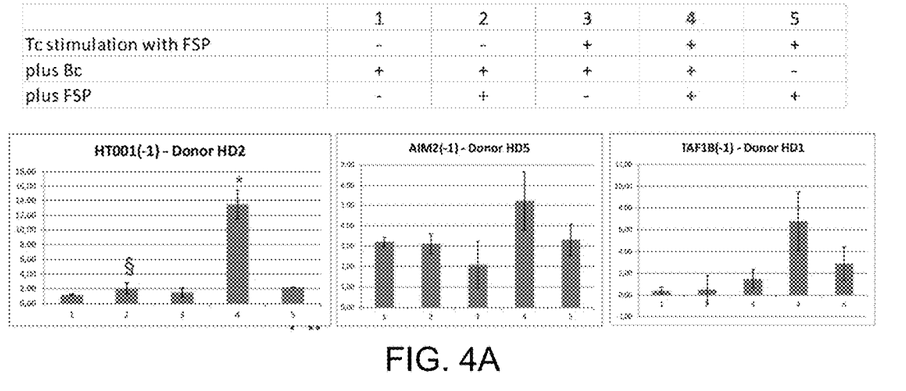
Figure 4B:
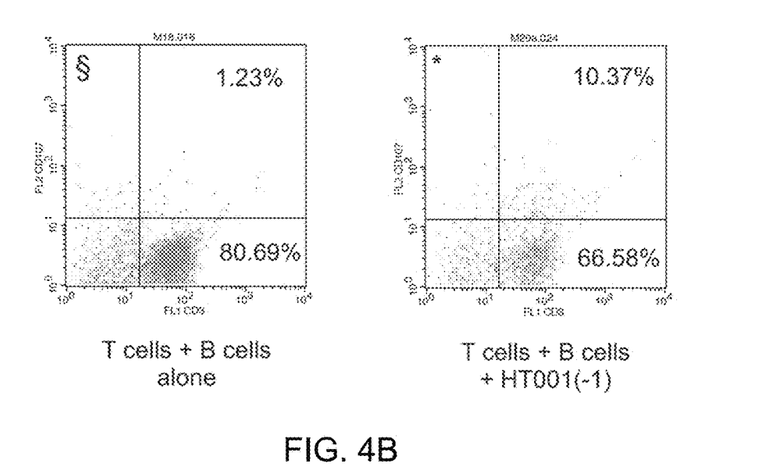

Cytotoxic responses as determined by CD107a surface expression were observed for T cells coincubated with B cells as antigen-presenting cells in the presence of the antigenic FSP (FIG. 4A). Significant responses were observed in different healthy donors after stimulation of T cells with the antigen for four weeks. Representative responses are shown in bar graphs. FIG. 4B shows representative FACS analysis of CD107a assay for T cells incubated with B cells as antigen-presenting cells in the absence (left panel) or presence (right panel) of the FSP antigen HT001(-1).

REFERENCES

Cunningham and Wells, Science 244 (1989), 1081-1085.
Fingl et al., The Pharmacological Basis of Therapeutics, Goodman and Gilman, eds. Macmillan Publishing Co., New York, pp. 1-46 (1975).
Kloor M, Michel S, von Knebel Doeberitz M. Immune evasion of microsatellite unstable colorectal cancers. Int J Cancer. 2010 Mar. 2. [Epub ahead of print]
Linnebacher M, Gebert J, Rudy W, Woerner S, Yuan Y P, Bork P, von Knebel Doeberitz M. Frameshift peptide-derived T-cell epitopes: a source of novel tumor-specific antigens. Int J Cancer. 2001 Jul. 1; 93(1):6-11.
Reuschenbach M, Waterboer T, Wallin K L, Einenkel J, Dillner J, Hamsikova E, Eschenbach D, Zimmer H, Heilig B, Kopitz J, Pawlita M, von Knebel Doeberitz M, Wentzensen N. Characterization of humoral immune responses against p16, p53, HPV16 E6 and HPV16 E7 in patients with HPV-associated cancers. Int J Cancer. 2008 Dec. 1; 123(11):2626-31.
Reuschenbach M, Kloor M, Morak M, Wentzensen N, Germann A, Garbe Y, Tariverdian M, Findeisen P, Neumaier M, Holinski-Feder E, von Knebel Doeberitz M. Serum antibodies against frameshift peptides in microsatellite unstable colorectal cancer patients with Lynch syndrome. Fam Cancer. 2009 Dec. 2. [Epub ahead of print]
Ripberger E, Linnebacher M, Schwitalle Y, Gebert J, von Knebel Doeberitz M. Identification of an HLA-A0201-restricted CTL epitope generated by a tumor-specific frameshift mutation in a coding microsatellite of the OGT gene. J Clin Immunol. 2003 September; 23(5):415-23.
Schwitalle Y, Kloor M, Eiermann S, Linnebacher M, Kienle P, Knaebel H P, Tariverdian M, Benner A, von Knebel Doeberitz M Immune response against frameshift-induced neopeptides in HNPCC patients and healthy HNPCC mutation carriers. Gastroenterology. 2008 April; 134(4):988-97.

Schwitalle Y, Linnebacher M, Ripberger E, Gebert J, von Knebel Doeberitz M. Immunogenic peptides generated by frameshift mutations in DNA mismatch repair-deficient cancer cells. Cancer Immun. 2004 Nov. 25; 4:14.

The invention is further described by the following numbered paragraphs:

1. A vaccine containing an MSI-specific frameshift peptide (FSP) wherein said FSP is capable of eliciting an immune response against tumors showing MSI.

2. The vaccine of paragraph 1 containing (a) an FSP comprising the following amino acid sequence:

```
(TAF1B(-1))
                                           (SEQ ID NO: 1)
NTQIKALNRGLKKKTILKKAGIGMCVKVSSIFFINKQKP;

(HT001(-1))
                                           (SEQ ID NO: 2)
EIFLPKGRSNSKKKGRRNRIPAVLRTEGEPLHTPSVGMRETTGLGC;

(AIM2(-1))
                                           (SEQ ID NO: 3)
HSTIKVIKAKKKHREVKRTNSSQLV;
Or (TGFBR2(-1))
                                           (SEQ ID NO: 4)
ASPKCIMKEKKSLVRLSSCVPVALMSAMTTSSSQKNITPAILTCC;
or
```

(b) a functional equivalent of an FSP of (b) which is still capable of eliciting an immune response against cancer showing MSI; or (c) a combination of FSPs of (a) and/or (b).

3. The vaccine of paragraph 1 or 2, wherein the FSP additionally contains a Tag sequence.

4. A vaccine containing a nucleic acid sequence encoding the FSP of any one of paragraphs 1 to 3 or a vector containing said nucleic acid sequence.

5. The vaccine of paragraph 4, wherein said vector is a plasmid or viral vector.

6. The vaccine of paragraph 5, wherein said viral vector is a poxvirus, adenovirus, retrovirus, herpesvirus, alphavirus-based vector or adeno-associated virus (AAV).

7. The vaccine of paragraph 6, wherein said poxvirus is a vaccinia virus, NYVAC, avipox virus, canarypox virus, ALVAC, ALVAC(2), fowlpox virus or TROVAC.

8. The vaccine of any one of paragraphs 1 to 7 additionally comprising an adjuvant and/or immunostimulatory cytokine or chemokine.

9. The vaccine of any one of paragraphs 1 to 8, wherein the active compound is presented in an oil in water or a water in oil emulsion vehicle.

10. The vaccine of any one of paragraphs 1 to 9 additionally comprising one or more other antigens.

11. The vaccine according to any one of paragraphs 1 to 10 for use in a method for the prevention or treatment of a tumor.

12. Use of the MSI tumor specific frameshift peptide (FSP) as defined in any one of paragraphs 1 to 3, the nucleic acid as defined in paragraph 4, or the vector as defined in any one of paragraphs 4 to 7 for the preparation of a vaccine for the prevention or treatment of a tumor.

13. The use according to paragraph 11 or 12 for preventive vaccination of high risk groups.

14. Use according to any one of paragraphs 11 to 13, wherein the tumor is colorectal cancer, endometrial cancer, gastric cancer or small bowel cancer.

15. Use according to paragraph 14, wherein the colorectal cancer is hereditary non-polyposis colorectal cancer (HNPCC).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A vaccine comprising:

(a) a MSI-specific frameshift peptide (FSP) wherein said FSP is capable of eliciting an immune response against tumors showing MSI, and wherein said FSP is selected from the group consisting of the following amino acid sequences:

```
                                           (SEQ ID NO: 1)
NTQIKALNRGLKKKTILKKAGIGMCVKVSSIFFINKQKP
(TAFIB(-1));

(SEQ ID NO: 2)
EIFLPKGRSNSKKKGRRNRIPAVLRTEGEPLHTPSVGMRETTGLGC
(HT001(-1));
and (SEQ ID NO: 3)
HSTIKVIKAKKKHREVKRTNSSQLV (AIM2(-1));
``` and (b) a compound selected from the group consisting of an adjuvant, immunostimulatory cytokine and chemokine.

2. The vaccine of claim 1, comprising a FSP and an adjuvant, wherein the adjuvant is selected from the group consisting of a salt of aluminium, salt of calcium, salt of iron, salt of zinc, an insoluble suspension of acylated tyrosine, an insoluble suspension of acetylated sugars, catonically derivatised polysaccharides, anionically derivatised polysaccharides, polypphospazenes and CpG containing oligonucleotides.

3. The vaccine of claim 1 comprising a combination of FSPs selected from SEQ ID NOs:1-3.

4. The vaccine of claim 3, wherein the FSPs consist of the FSPs of SEQ ID NOs:1-3.

5. The vaccine of claim 1, wherein the FSP additionally contains a Tag sequence.

6. The vaccine of claim 1, wherein the FSP is presented in an oil in water or a water in oil emulsion vehicle.

7. The vaccine of claim 1, wherein the vaccine additionally comprises one or more other antigens.

* * * * *

SEQUENCE LISTING

```
<160> NUMBER OF SEQ ID NOS: 11

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Asn Thr Gln Ile Lys Ala Leu Asn Arg Gly Leu Lys Lys Lys Thr Ile
1               5                   10                  15

Leu Lys Lys Ala Gly Ile Gly Met Cys Val Lys Val Ser Ser Ile Phe
            20                  25                  30

Phe Ile Asn Lys Gln Lys Pro
        35

<210> SEQ ID NO 2
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

```
Glu Ile Phe Leu Pro Lys Gly Arg Ser Asn Ser Lys Lys Gly Arg
1               5                   10                  15

Arg Asn Arg Ile Pro Ala Val Leu Arg Thr Glu Gly Glu Pro Leu His
            20                  25                  30

Thr Pro Ser Val Gly Met Arg Glu Thr Thr Gly Leu Gly Cys
        35                  40                  45

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ser Thr Ile Lys Val Ile Lys Ala Lys Lys His Arg Glu Val
1               5                   10                  15

Lys Arg Thr Asn Ser Ser Gln Leu Val
            20                  25

<210> SEQ ID NO 4
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ser Pro Lys Cys Ile Met Lys Glu Lys Lys Ser Leu Val Arg Leu
1               5                   10                  15

Ser Ser Cys Val Pro Val Ala Leu Met Ser Ala Met Thr Thr Ser Ser
            20                  25                  30

Ser Gln Lys Asn Ile Thr Pro Ala Ile Leu Thr Cys Cys
        35                  40                  45

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(24)

<400> SEQUENCE: 6 aag gaa aaa aaa aag cct ggt gag                                      24
Lys Glu Lys Lys Lys Pro Gly Glu
1               5
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Glu Lys Lys Lys Pro Gly Glu
1               5

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(21)

<400> SEQUENCE: 8 aag gaa aaa aaa agc ctg gtg ag                                      23
Lys Glu Lys Lys Ser Leu Val
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Lys Glu Lys Lys Ser Leu Val
1               5

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(18)

<400> SEQUENCE: 10 aag gaa aaa aaa gcc tgg tgag                                        22
Lys Glu Lys Lys Ala Trp
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Glu Lys Lys Ala Trp
1               5